US006165126A

United States Patent [19]
Merzenich et al.

[11] Patent Number: 6,165,126
[45] Date of Patent: Dec. 26, 2000

[54] REMEDIATION OF DEPRESSION THROUGH COMPUTER-IMPLEMENTED INTERACTIVE BEHAVIORAL TRAINING

[75] Inventors: Michael M. Merzenich; David T. Blake, both of San Francisco, Calif.

[73] Assignees: Scientific Learning Corporation, Berkeley; The Regents of the University of California, Oakland, both of Calif.

[21] Appl. No.: 09/153,568

[22] Filed: Sep. 15, 1998

Related U.S. Application Data

[63] Continuation of application No. 09/134,759, Aug. 14, 1998.
[51] Int. Cl.[7] .................................................. A61B 19/00
[52] U.S. Cl. ............................................................ 600/300
[58] Field of Search .................................... 600/300, 301, 600/544, 545; 128/904, 905, 920–924

[56] References Cited

U.S. PATENT DOCUMENTS

| 5,678,571 | 10/1997 | Brown | 128/898 |
|---|---|---|---|
| 5,722,418 | 3/1998 | Bro | 600/300 |
| 5,725,472 | 3/1998 | Weathers | 600/21 |
| 5,910,107 | 6/1999 | Iliff | 600/300 |
| 5,913,310 | 6/1999 | Brown | 128/897 |

FOREIGN PATENT DOCUMENTS

| WO 93/02622 | 2/1993 | WIPO . |
|---|---|---|
| WO 94/04072 | 3/1994 | WIPO . |
| WO 94/06088 | 3/1994 | WIPO . |
| WO 95/29447 | 11/1995 | WIPO . |
| WO 97/06730 | 2/1997 | WIPO . |
| WO 97/34526 | 9/1997 | WIPO . |

OTHER PUBLICATIONS

Frith, C., The role of the prefrontal cortex in self–consciousness: the case of auditory hallucinations, pp. 1505–1512 (1996).

Roger Jelliffe, et al., Adaptive control of drug dosage regimens: basic foundations, relevant issues, and clinical examples, International Journal of Bio–Medical Computing 36, (pp. 1–23), © 1994.

Schneider et al. Self–Regulation of Slow Cortical Potentials in Psychiatric Patients: Schizophrenia, © Dec. 1992, Biofeedback and Self–Regulation, vol. 17, No. 4, pp. 277–292.

Tretter F., Perspectives of Computer–Aided Therapy and Rehabilitation in Psychiatry, Jul. 1996, pp. 475–486.

Hermanutz M. and Gestrich J., Computer–assisted Attention Training in Schizophrenics, 1991, European Archives of Psychiatry and Clinical Neuroscience, vol. 240, pp. 282–287, Dec. 1991.

Stanley V. Catts, M.D. et al., "Brain Potential Evidence for an Auditory Sensory Memory Deficit in Schizophrenia", Am J Psychiatry 152:2; Feb. 1995, pp. 213–219.

U. Schall et al., "A left temporal lobe impairment of auditory information processing in schizophrenia: an event–related potential study", © 1997 Elsevier Science Ireland Ltd., Neuroscience Letters 229, pp. 25–28.

(List continued on next page.)

*Primary Examiner*—Samuel G. Gilbert
*Attorney, Agent, or Firm*—Beyer Weaver & Thomas, LLP

[57] ABSTRACT

A computer-implemented technique for remediating depression in a person which includes assessing, using a computer-implemented interactive behavioral assessment regime, a depression index for the person. If the depression index is above a predefined benchmark, the computer-implemented technique includes periodically reassessing the depression index by waiting for at least a predefined period of time, and performing the above assessing step after the predefined period of time expires. If the depression index is below the predefined benchmark, treating the person by administering computer-implemented interactive behavioral training to the person. The computer-implemented interactive behavioral training is sufficiently intensive during each training day to create a permanent change in modulatory functions of neurotransmitters of one of norepinephrine and serotonin in the person.

37 Claims, 4 Drawing Sheets

OTHER PUBLICATIONS

Michael F. Green Ph.D. et al., "Backward Masking Performance in Unaffected Siblings of Schizophrenic Patients—Evidence for a Vulnerability Indicator", Arch Gen Psychiatry, vol. 54, May 1997, pp. 465–472.

Kristin S. Cadenhead et al., "The Relationship of Information–Processing Deficits and Clinical Symptoms in Schizotypal Personality Disorder", © 1996 Society of Biological Psychiatry, vol. 40, pp. 853–858.

Sören Nielzén et al., "Perceptual Grouping due to Pitch and Amplitude in Hallucinating Schizophrenics", Psycopathology 1997, vol. 30, pp. 140–148.

Lynn E. DeLisi et al., "Schizophrenia as a chronic active brain process: a study of progressive brain structural change subsequent to the onset of schizophrenia", © 1997 Elsevier Science Ireland Ltd., Nuroimaging Section 74, pp. 129–140.

Sandra S. Kindermann et al., "Review of functional magnetic resonance imaging in schizophrenia", © 1997 Elsevier Science B.V., Schizophrenia Research 27, pp. 143–156.

Steven M. Silverstein et al., "Reduced Top–Down Influence in Auditory Perceptual Organization in Schizophrenia", Journal of Abnormal Psychology 1996., vol. 105, No. 4, pp. 663–667.

James Seltzer, Ph.D. et al., "Neuropsychological Rehabilitation in the Treatment of Schizophrenia", Connecticut Medicine, Sep. 1997, vol. 61, No. 9, pp. 597–608.

Theodore Van Putten, M.D. et al., "Plasma Homovanillic Acid as a Predictor of response to Fluphenazine Treatment", Psychopharmacology Bulletin, vol. 1, 1989, pp. 89–91.

Masataka Watanabe et al., "Increase of extracellular Dopamine in Primate Prefrontal Cortex During a Working Memory Task", © 1997 The American Physiological Society, pp. 2795–2797.

Bruce E. Wexler et al., "Normal neurocognitive performance after extended practice in patients with schizophrenia", © 1997 Elsevier Science B.V., pp. 173–180.

Graham V. Williams et al., "Modulation of memory fields by dopamine D1 receptors in prefrontal cortex", Nature, vol. 376, Aug. 17, 1995, pp. 572–575.

Daniel S. O'Leary, Ph.D. et al., "Auditory Attentional Deficits in Patients with Schizophrenia—A Positron Emission Tomography Study", Arch Gen Psychiatry, vol. 53, Jul. 1996, pp. 633–641.

Dean F. Salisbury et al., "The N2 event–related potential reflects attention deficit in schizophrenia", Elsevier Science B.V., Biological Psychology 39, 1994, pp. 1–13.

Karen Shedlack et al., "Language processing and memory in ill and well siblings from multiplex families affected with schizophrenia", © 1997 Elsevier Science B.V., vol. 25, pp. 43–25.

Colin D. Field et al., "Computer–Aided Cognitive Rehabilitation: Possible Application To The Attentional Deficit Of Schizophrenia, A Report Of Negative Results", © Perceptual and Motor Skills 1997, vol. 85, pp. 995–1002.

Michael F. Green Ph.D., "What Are the Functional Consequences of Neurocognitive Deficits in Schizophrenia?", Am J Psychiatry 153:3, Mar. 1996, pp. 321–330.

M. Hermanutz et al, "Computer–assisted Attention Training in Schizophrenics—A Comparative Study", © Springer–Verlag 1991, European Archives of Psychiatry and clinical Neuroscience 1991, pp. 282–287.

Amy R. Koreen, M.D., et al., "Plasma Homovanillic Acid Levels in First–Episode Schizophrenia—Psychopathology and Treatment Response", Arch Gen Psychiatry, vol. 51, Feb. 1994, pp. 132–138.

Heidi Nisbet et al., "Improving Schizophrenic in–patients' Wisconsin card–sorting performance", © 1996 The British Psychological Society, British Journal Of Clinical Psychology (1996) vol. 35, pp. 631–633.

Toshiyuki Sawaguchi et al., "The Role of D1–Dopamine Receptor in Working Memory: Local Injections of Dopamine Antagonists Into the Prefrontal Cortex of Rhesus Monkeys Performing an Oculomotor Delayed–Response Task", Journal of Neurophysiology, Feb. 1994, pp. 515–528.

Andrew J. Saykin, PsyD. et al., "Neuropsychological Deficits in Neuroleptic Naïve Patients with First–episode Schizophrenia", Arch Gen Psychiatry, vol. 51, Feb. 1994, pp. 124–131.

Wolfram Schultz et al., "A Neural Substrate of Prediction and Reward", Science, vol. 275, Mar. 14, 1997, www-.sciencemag.org, pp. 1593–1599.

Andrew J. Saykin, PsyD, et al., "Neuropsychological Function in Schizophrenia–Selective Impairment in Memory and Learning", Arch Gen Psychiatry, vol. 48, Jul. 1991, pp. 618–624.

Bruce E. Wexler, M.D., et al., "The Outpatient Treatment of Depression Implications of Outcome Research for Clinical Practice", The Journal of Nervous and Mental Disease, vol. 180, No. 5, May 1992, pp. 277–286.

Ralph H.B. Benedict, et al., "Effects of Attention Training on Information Processing Schizophrenia", Schizophrenia Bulletin, vol. 20, No. 3, 1994, pp. 537–546.

Patrick W. Corrigan, et al., "Memory and vigilance training to improve social perception in schizophenia", Schizophrenia Research, © 1995 Elsevier Science B.V., pp. 257–265.

Ian Creese, et al., "Dopamine Receptor Binding Predicts Clinical and Pharmacological Potencies of Antischizophrenic Drugs", © 1976 American Assoc. for the Advancement of Science, Apr. 30, 1976, vol. 192, pp. 481–483.

Ian Creese, et al., "Dopamine Receptors: A Classification", Dept. of Neurosciences, Journal of Clinical Psychopharmacology, © 1982 Williams & Wilkins Co., vol. 2, No. 5, pp. 329–335.

Ricardo Davila, PhD, et al., "Plasman Homovanillic Acid as a Predictor of Response to Neuroleptics", Arch Gen. Psychiatry, vol. 45, Jun. 1988, pp. 564–567.

Ann Delahunty, PhD., et al., "Rehabilitation of frontal/ executive impairments in schizophrenia", Australian and New Zealand Journal Of Psychiatry, vol. 30, No. 6, Dec. 1996, pp. 760–767.

Nagarajan et al., "Practice–Related Improvements in Somatosensory Interval Discrimination Are Temporally Specific But Generalize Across Skin Location, Hemisphere, and Modality," Feb. 15, 1998, The Journal of Neuroscience, pp. 1559–1570.

Merzenich et al., "Temporal Processing Deficits of Language–Learning Impaired Children Ameliorated by Training," Jan. 5, 1996, Science vol. 271, pp. 77–81.

REMEDIATION OF DEPRESSION THROUGH COMPUTER-IMPLEMENTED INTERACTIVE BEHAVIORAL TRAINING

This application is a continuation of a U.S. Patent Application entitled "Prophylactic Reduction and Remediation of Schizophrenic Impairments Through Interactive Behavioral Training" by Michael M. Merzenich, filed on Aug. 14, 1998 (U.S. application Ser. No. 09/134,759), which is incorporated by reference herein.

BACKGROUND OF THE INVENTION

The present invention relates to computer-implemented interactive training techniques for treating depression. More specifically, the present invention relates to intensive computer-implemented behavioral training techniques that effectively remediate symptoms of clinical depression and of depressive personality disorders.

Depression in its manifold specific forms is the most common form of diagnosed mental illness. Although the symptoms may vary in different individuals, a common distinction between depressives differentiates 'unipolar' from 'bipolar' individuals. The former have a single-polar (depressed) disorder of mood. The latter swing alternatively (commonly with a cycle period of days to weeks in duration) between depression and mania. Within these simple distinctions and under the broad umbrella term 'depression' fall many depression subtypes and an overlapping classification of an often-milder 'depressive personality'.

There are many thousands of published reports on the epidemiology, neurology, and treatment of this commonly occurring illness, and many thousands more publications relate to the study of its underlying neurology. Generally speaking, there are two primary treatment strategies that have been effective for very large populations of depressives. These two primary treatment strategies involve pharmacological therapies and psychological therapies. Generally speaking, there are three primary treatment strategies that have been effective for large populations of depressives. These three treatments are pharmacotherapy, psychotherapy, and electro-convulsive therapy.

The pharmacological treatment of depression most commonly involves application of a drug that partially blocks the extracellular-to-intracellular re-uptake of the brain transmitter serotonin, thereby increasing available serotonin levels at its normal extra-cellular site of action. Equally effective anti-depressive effects have been observed when the re-uptake of the brain transmitter norepinephrine is partially blocked. Both actions are believed to increase the active quantities of these neurotransmitters in synaptic zones, which are their main sites of effect, which in turn appears to alleviate the symptoms of depression.

It is believed that anti-depressive medications can also result in the elaboration of the cortical terminals of norepinephrine-containing neurons that have their cell bodies within the locus coeruleus, the small brainstem nucleus that contains all of the NE cells that project to the cerebral cortex. It is noted that those cortical terminals tend to be more sparse in animal models of depression. Neuron numbers in this nucleus also tend to be smaller in number in depressed patients who commit suicide. On the other hand, neurons in this nucleus and their terminal arbors in the cortex have been shown to be capable of being physically regeneratively invigorated and elaborated by drug treatment that results in the more normal reengagement of this critical modulatory control system.

It is noted, however, that while drug treatment 'overcomes' depression, there are commonly underlying residual behavioral differences between depressives and normals that are not impacted by the pharmacological treatment. For example, in a standard index of depression symptoms, abnormal responses to danger and willingness to make a novel choice are two measures of depression. As another example, with treatment with fluoxetine (Prozac), the former measure (which is likely more directly related to serotonin level imbalance and drug-induced correction) is improved, while the latter measure (which is likely more directly related to norepinephrine level imbalances) is not.

As mentioned earlier, psychological therapies represent an important form of treatment for depressives. Psychotherapy and related widely applied therapies (e.g., meditation training) plausibly have their primary impacts through quieting and calming the patient, i.e., in relieving underlying chronic and episodic impacts of stress, which is believed to be a contributor to depression. In the past, psychotherapies typically involve weekly hour long sessions with a therapist that focus on one of three strategies: behavioral changes, cognitive changes, or social changes in the patient. These weekly sessions last three to four months, after which the patient improvement may be comparable to pharmacotherapy. Each of the psychotherapies focuses on discussing changes that the patient is expected to self-implement for the rest of the week. For instance, one type of behavioral psychotherapy has the patient itemize things associated with harm and things associated with reward. The patient is then instructed to seek out things that are rewarding while minimizing exposure to things that evoke fear responses. The goal is for the patient to have some control over his environment.

Electroconvulsive treatment is generally found effective in older subjects who do not respond well to pharmacotherapies. A series of electrical 'shocks' are delivered to the temples of the subjects in each session, and subjects, with a high probability, begin to feel better after several weekly sessions. It should also be noted that a substantial subpopulation of depressed patients are resistant to any or all of the pharmacological, psychotherapeutic, and electroconvulsive treatments, and that persistence of symptoms and relapse are common.

In view of the foregoing, there are desired therapeutic techniques that can remediate depression or prevent its onset without introducing unwanted side effects. In particular, there are desired depression treatments, prophylactic or otherwise, that do not require or that reduce the need for anti-depressive medication or psychotherapy.

SUMMARY OF THE INVENTION

The invention relates, in one embodiment, to a technique for assessing and remediating depression using intensive operant computer implemented interactive behavioral training exercises. The computer implemented interactive behavioral training exercises are designed to remediate the symptoms of clinical depression and of depressive personality disorder by upregulating the trial-by-trial and daily accumulative cortical levels of norepinephrine and serotonin, and to indirectly reestablish more normal modulatory functions of these critical neurotransmitters, as well as of dopamine (and) acetycholine and other modulatory neurotransmitters contributing to the control of learning, operational behavioral status, and mood. In accordance with one aspect of the present invention, this is achieved by intensively engaging the depressed subject (e.g., for many tens of minutes/day) in behaviors that directly augment the behaviorally appropriate release of these target neurotransmitters, and through enduring plastic neurological changes, that increase the activities and physical status of neurons that distribute these neurotransmitters to the forebrain in normal behaviors.

In one embodiment, the invention relates to a computer-implemented technique for remediating depression in a person which includes assessing, using a computer-implemented interactive behavioral assessment regime, a depression index for the person. If the depression index is above a predefined benchmark, the computer-implemented technique includes periodically reassessing the depression index by waiting for at least a predefined period of time, and performing the above assessing step after the predefined period of time expires. If the depression index is below the predefined benchmark, treating the person by administering computer-implemented interactive behavioral training to the person. The computer-implemented interactive behavioral training is sufficiently intensive during each training day to create a permanent change in modulatory functions of neurotransmitters of one of norepinephrine and serotonin in the person.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which like reference numbers refer to like items and in which.

DETAILED DESCRIPTION OF THE PREFERRED EMBODIMENTS

Figure 1A:
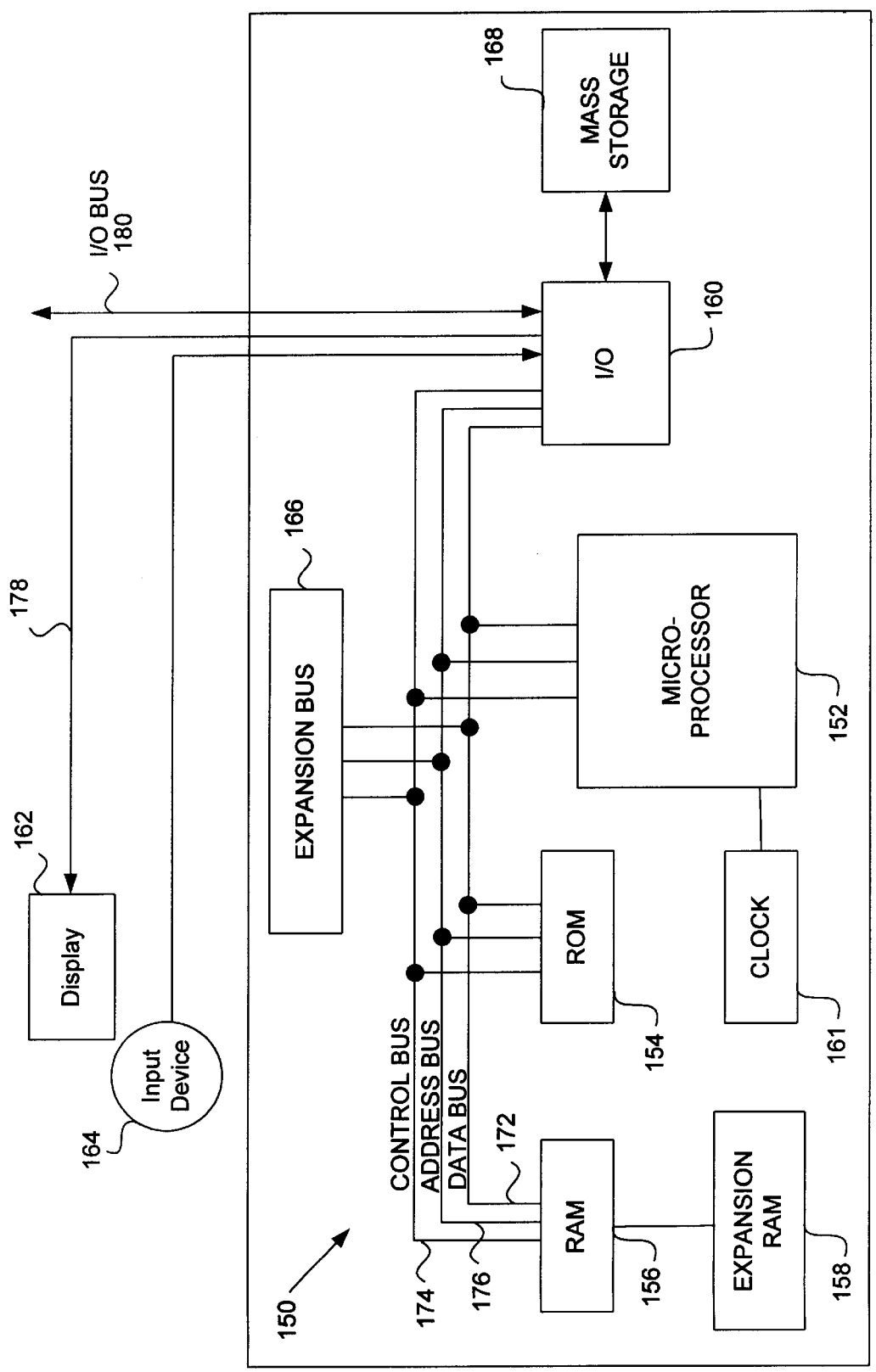
FIGS. 1A and 1B illustrate, in accordance with one embodiment of the invention, the computer-controlled apparatus for administering interactive behavioral exercises that remediate depression.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

A. Theories

Studies of depressives have suggested that their behavioral deficits are generally consistent with symptoms of lower (depressed) norepinephrine and usually lower (but sometimes higher) serotonin activity in the forebrain. In general, depressives tend to be poor performers at cognitively demanding tasks. By way of example, depressives tend to be poor performers at responding appropriately to unexpected or novel stimulus events, at responding appropriately to fearful stimuli, at accepting negative or punishing feedback in task performance, and at sustaining high performance levels in an attentively demanding task.

Depressed individuals also tend to have impairments in learning and memory in operations that require vigilance and short-term memory. The operations are, for example, correctly responding to specific words or phrases or verbal concepts that are being vigilantly listened for in ongoing speech, correctly responding to specific images or objects or visual concepts that they are vigilantly looked for in ongoing vision, and remembering and operating on sentences, word series, number series, object series or other similar stimulus sets in task that require their short-term memorization. Their fastest responses in such tasks are consistently slower than are the responses of normal individuals. Further, depressed individuals tend to have abnormal brain responses that parallel these differences in response to novel stimuli, and to the adaptation to new stimuli. Examples of these evoked brain responses include an abnormal adaptation of brain signals to repetitive stimuli, an abnormally weak response signaling unexpected or novel stimuli, among others.

Studies also show that depressives tend to have depressed activities in areas that are associated with novelty, vigilance, and short-term memory in the forebrain, specifically the anterior cingulate and lateral prefrontal cortex, and in the amygdala, which contributes to mood and fear-related (fight/flight) response control.

It has been observed that the response ("reaction") times in short-term memory and vigilance tasks are longer in depressives than in normals. As the terms are used herein, short term memory tasks refer to tasks in which a stimulus is given and must be remembered for use more than one second later in the task, but less than a minute later. A specific, but not limiting, example of a short term memory task would be the digit span task. In this task, subjects are given a series of numbers, and asked to repeat them forward and backward. The subject's score depends on the length of the series that he can consistently repeat.

A vigilance task is a task in which the subject is searching for a target stimulus in a stream of distractors. A specific, but not limiting, example would be the continuous performance task. In the most general version of this task, subjects view a stream of single numbers, and are required to signal for every example of one specific number. Another version of a vigilance tasks requires a subject to find an oddball stimulus in a stream of repetitive non-target stimuli. The most consistent findings in psychophysical tests of depressives are I) slower reaction times in almost all circumstances II) impaired performance on tasks that involve both short term memory and reaction time and III) impaired performance and slower reaction times on tests of vigilance such as the continuous performance task or the oddball task. In summary, depressives tend to be uninterested in novel stimuli, and their overall arousal and reaction speed is suppressed.

It has also been observed that they have a heightened sensitivity to fear-inducing stimuli. This state reflects an exaggerated neurological form of a normal response to stress, in which the brain adopts an instinctively more defensive behavioral strategy, and suppresses its responses to novel stimuli and in effect loses its interest in activities that do not relate directly to the stress-inducing (life-threatening) inputs.

Studies have also suggested that there are several common features shared by locus coeruleus and raphe nucleus neurons that deliver norepinephrine and serotonin to the cortex, respectively. Both are believed to play a role in behavioral learning. The locus coeruleus may be implicated in the signaling of novelty and in the maintenance of vigilance in learning. The raphe nucleus may be implicated in the contextual control of fear (flight) reactions, and in the control of the overall state of arousal and activity by the forebrain. Thus, both contribute to the 'arousal' and 'alertness' that sustains normal alertness and wakefulness.

It is also believed that locus coeruleus and raphe nucleus neurons receive projections originating from the endocrine system that result in corticosterone-mediated effects within them. Corticosterones are powerful steroids released by the endocrine gland system in response to danger or stress. The control of the release of norepinephrine (noradrenaline or adrenaline), serotonin, dopamine and other neurotransmitters in the body and brain has many strong effects that are adaptive for appropriately responding to great danger or stress. This powerful signaling system strongly modulates activity consistent with an appropriate brain response in the face of stress or danger, for example, a state of high alertness and heightened preparations for very fast response, while longer term processes like learning or memory or making long term decisions or sophisticated perceptual or cognitive judgments are suppressed. Thus, stress contributes importantly to the genesis of depression in the majority of affected patients, in large part through these (and other related) effects.

Studies conducted in the locus coeruleus show that it tends to be engaged specifically by novel stimuli, with responses adapting quickly as stimuli become familiar. The locus coeruleus also tends to be engaged in a vigilance task in which an animal is looking for a specific stimulus presented among other non-target stimuli. The responses of neurons within the nucleus tend to grow progressively with vigilance training, as the animal comes to more reliably detect a target stimulus. When the vigilance target is changed to a stimulus that the animal was not previously responding to, it is observed that neurons in the locus coeruleus come to respond vigorously, over time, to every presentation of this new target.

It has been observed that neurons in the locus coeruleus tend to respond vigorously when vigilance-based or novelty-based responses are rewarded in a behavioral trial. The marked functional plasticity of locus coeruleus neurons expressed by these findings and the marked capacity for activity-based elaboration of the projections of these neurons to the cerebral cortex are an important starting point in the design of the present novel, intensive behavioral training-based remediative therapy for the treatment of depression. That strategy, outlined in broad terms below, is motivated by an understanding of the fundamental neurology of the illness and by our knowledge about powerful brain plasticity mechanisms that contribute to its expression and genesis. The approach outlined here is unique in the specific nature of training employed, in the direct targeting in training of restoring more normal neurotransmitter (e.g., norepinephrine, serotonin, dopamine, acetylcholine, endogeneous opioid) release, in the intensity with which it must be applied to be reliably successful, in the specific design of behavioral tasks used in this intensive training, and in its use of built-in compliance and performance monitoring tools applied to effectively control training, and to insure enduring positive training effects.

B. General Philosophy of the Inventive Technique

From the foregoing, it is believed that depression may be remediated by engaging the subject in intensive operant computer guided interactive behavioral training exercises designed to remediate the symptoms of clinical depression and of depressive personality disorder. Based on studies of the plasticity of the locus coeruleus and raphe nucleus, on the actions of neuromodulatory transmitters distributed widely to the forebrain from those nuclei, and on understanding of the abnormal behaviors and brain pathologies in depressed patients, one of the objectives of these training exercises is to upregulate the trial-by-trial and daily accumulative cortical levels of norepinephrine and serotonin, and to indirectly re-establish more normal modulatory functions of these critical neurotransmitters, as well as of dopamine (and) acetycholine and other modulatory neurotransmitters contributing to the control of learning, operational behavioral status, and mood. In accordance with one aspect of the present invention, this is achieved by intensively engaging the depressed subject (e.g., for many tens of minutes/day) in behaviors that directly augment the behaviorally appropriate release of these target neurotransmitters, and through enduring plastic neurological changes, that increase the activities and physical status of neurons that distribute these neurotransmitters to the forebrain in normal behaviors.

In accordance with another aspect of the present invention, the content of these intensive training exercises is preferably designed to calm and quiet the patient, to reduce the contribution of stress, which is believed to be a powerful contributor to depression origin and expression. Further, the interactive behavioral exercises are designed so that the subject is rewarded (i.e., for being correct) in a majority of the trials. Preferably, the exercises are configured such that the subjects can respond correctly and be rewarded at least 50% and more preferably at least about 80% of the trials attempted.

In general, an objective of the interactive behavioral exercise training regime is to re-enliven the cerebral cortex through intensive daily training to improve its overall level of arousal, thus normalizing its response to novel stimuli. In so doing, the intensive interactive behavioral training exercises seek to re-establish the depressives' normal ability to respond to stimuli with high vigilance, which results in improvements in response ("reaction" time); and re-invigorate it to respond strongly and consistently to goal-directed behaviors.

Additionally, another equally important objective of the interactive behavioral exercise training regime is to re-establish more normal levels of expression and to reestablish more normal stimulus-by-stimulus actions of norepinephrine, serotonin and related neuromodulatory transmitters (aceylcholine, dopamine, endogeneous opioids).

Still further, another objective of the interactive behavioral exercise training regime is to calm and quiet the patient while they are being invigorated mentally, by employing the strongest possible level of positive reinforcement and with a content in exercises that powerfully favors positive and calming content over negative and fearful content, to ameliorate the contributions of stress to long-term neuropathology.

C. Exemplary Implementations

Figure 1B:
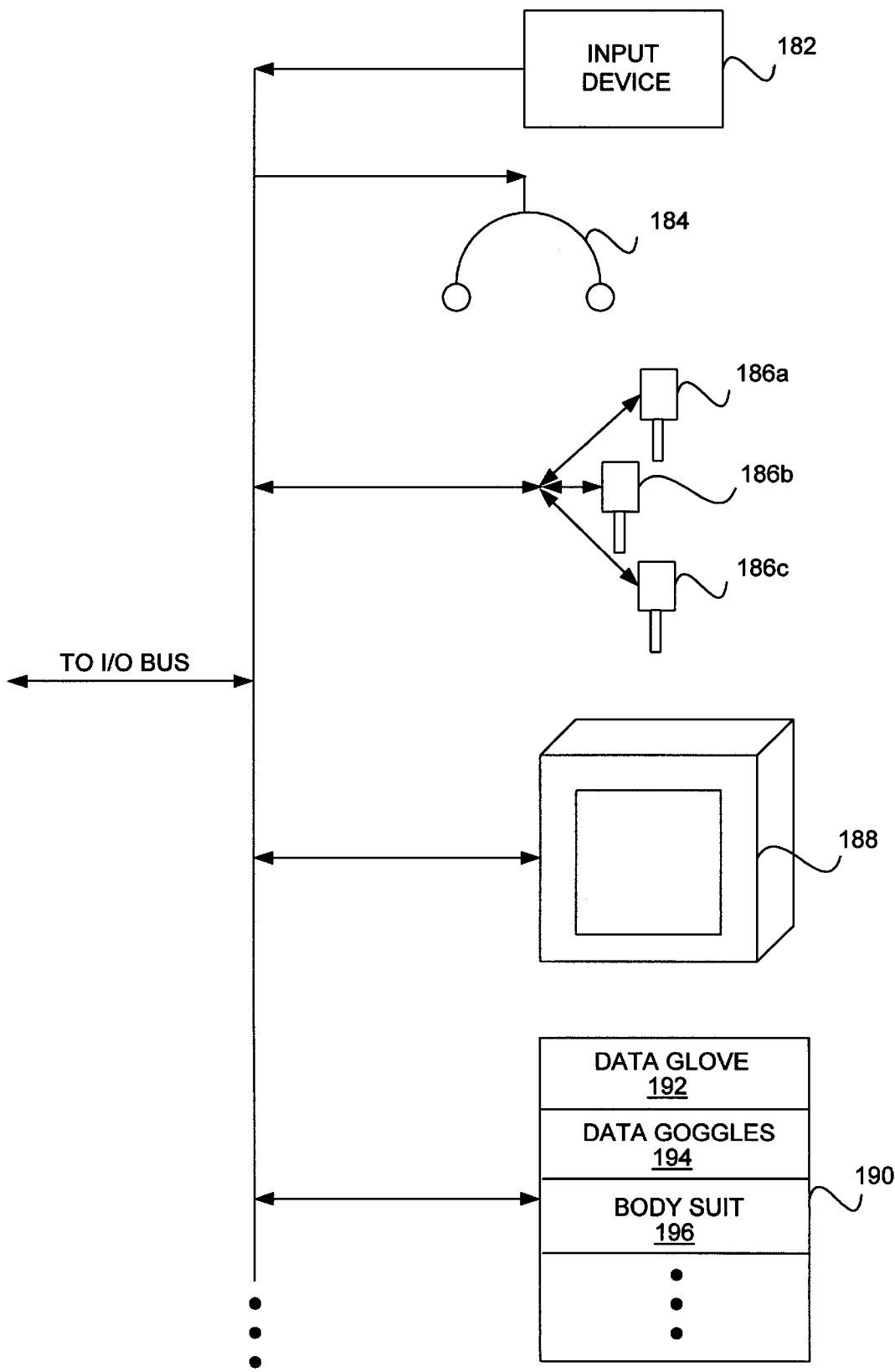

The features and advantages of these aspects of the invention, as well as other aspects of the present invention, may be better understood with reference to the figures and discussions that follow. As mentioned earlier, the depression assessment and prevention/remediation exercises of the present invention are preferably implemented using computer-based apparatus. FIGS. 1A and 1B illustrate, in accordance with one embodiment of the invention, an exemplary computer-controlled apparatus, including computer 150, for delivering computer-controlled stimuli to the subject, to receive responses from the subject, and to provide feedback pertaining to performance to the subject in an interactive behavioral training program designed to remediate depression.

Referring to FIG. 1A, a computer system 150 in accordance with the present invention includes a central processing unit (CPU) 152, read only memory (ROM) 154, random access memory (RAM) 156, expansion RAM 158, input/output (I/O) circuitry 160, display assembly 162, input device 164, and expansion bus 166. Computer system 150 may also optionally include a mass storage unit 168 such as a disk drive unit or nonvolatile memory such as flash memory and a real-time clock 161. In one embodiment, mass storage unit 168 may include units which utilize removable computer readable media, such as floppy disks, opto-magnetic media, optical media, and the like for the storage of programs and data.

CPU 152 is preferably a commercially available, single chip microprocessor such as one of the Intel X86 (including Pentium™ or PentiumII™) or Motorola 680XX family of chips, a reduced instruction set computer (RISC) chip such as the PowerPC$^a$ microprocessor available from Motorola, Inc., or any other suitable processor. CPU 152 is coupled to ROM 154 by a data bus 172, control bus 174, and address bus 176. ROM 154 may partially contain the basic operating system for the computer system 150. CPU 152 is also connected to RAM 156 by busses 172, 174, and 176 to permit the use of RAM 156 as scratch pad memory. Expansion RAM 158 is optionally coupled to RAM 156 for use by CPU 152. CPU 152 is also coupled to the I/O circuitry 160 by data bus 172, control bus 174, and address bus 176 to permit data transfers with peripheral devices.

I/O circuitry 160 typically includes a number of latches, registers and direct memory access (DMA) controllers. The purpose of I/O circuitry 160 is to provide an interface between CPU 152 and such peripheral devices as display assembly 162, input device 164, mass storage 168, and/or any other I/O devices. I/O circuitry 160 may also include analog-to-digital (A/D) converters, digital-to-analog (D/A) converters, as well as other control circuits for controlling and receiving feedback data from the I/O devices. The I/O devices suitable for generating stimuli to be administered to the test subject and for receiving responses therefrom may be coupled to I/O bus 180 of computer 150. They are discussed in greater detail with reference to FIG. 1B. Display assembly 162 of computer system 150 is an output device for displaying objects and other visual representations of data, as well as for generating visual stimuli in one embodiment.

The screen for display assembly 162 can be a device that uses a cathode-ray tube (CRT), liquid crystal display (LCD), or the like, of the types commercially available from a variety of manufacturers. Input device 164 can be a keyboard, a mouse, a stylus working in cooperation with a position-sensing display, or the like. Alternatively, input device 164 can be an embedded RF digitizer activated by an "active" RF stylus. As a further alternative, input device 164 may be any type of switch capable of communicating a test subjects response to computer system 150. Therefore, as used herein, the term input device will refer to any mechanism or device for entering data and/or pointing to a particular location on a screen of a computer display. One or more input devices may be provided to control computer 150 and/or to receive responses from the test subject. The aforementioned input devices are available from a variety of vendors and are well known in the art.

Some type of mass storage 168 is generally considered desirable. However, mass storage 168 can be eliminated by providing a sufficient amount of RAM 156 and expansion RAM 158 to store user application programs and data. In that case, RAMs 156 and 158 can optionally be provided with a backup battery to prevent the loss of data even when computer system 150 is turned off. However, it is generally desirable to have some type of long term mass storage 168 such as a commercially available hard disk drive, nonvolatile memory such as flash memory, battery backed RAM, PC-data cards, or the like.

In FIG. 1B, some exemplary stimuli generators are shown, including headphone 184 (for delivering auditory stimuli), computer-controlled probe 186 (for delivering touch stimuli), visual stimuli generator 188 (for delivering visual stimuli), and/or virtual reality apparatus 190 (for delivering stimuli to and receiving responses from the test subject in a virtual manner through any of the senses). In general, these I/O devices may interface with computer system 150 via I/O circuit 160 or an appropriate interface circuit, which may be external to computer 150 and/or dedicated to the I/O device. Visual stimuli generator 188 may represent, for example, any light generating device such as a light bulb, a flash device, another computer display screen or the like if such is employed instead of display screen 162 of computer 150 for providing visual stimuli to the test subject. Virtual reality apparatus 190 may include, for example data glove 192, virtual goggles 194, body suit 196, or the like, each of which may be able to both deliver the stimuli to the test subject as well as sense the responses therefrom. An optional input device 182 is also shown, representing a dedicated input device, such as a switch, for receiving responses from the test subject. Optional input device 182 is provided when it is desired to receive responses to the test stimuli from the test subject through an input device other than input device 164 of computer 150. Other optional devices (not shown) may also be provided and contain therein transducer to receive other types of responses from the subject. By way of example, a microphone may be provided to receive verbal responses from the client to be processed by the computer.

In operation, computer system 150 is employed to generate control signals to the stimuli generator(s) to produce the stimuli of the various tests. These stimuli are then finished to the test subject for training, and the responses from the test subject may then be recorded by input device 164 and/or input device 182 (or another suitable input device) and analyzed by CPU 152. If desired, feedback (both positive and negative with emphasis preferably on the positive) to the test subject may be given at various stages of the test(s) via, for example, display assembly 162.

It should be borne in mind that although computer system 150 is discussed in some detail herein to facilitate discussion, the invention itself may be practiced using a variety of suitable computer-implemented techniques. In general, any suitable computer system may be employed for generating control signals to the stimuli generators and receive feedback from the input device(s). Further, the inventive training technique disclosed herein may be implemented via a computer network, such as a local area network (LAN), wide area network (WAN) or a global computer network such as the Internet (also popularly known as "the Web"). In the latter cases, the inventive computer-implemented assessment and/or training technique may be implemented at least in part as downloadable computer software and/or data (e.g., applets such as JAVA™ applets from Sun Microsystems Inc.). The downloadable computer software and data may be kept on one or more servers on the network, accessible by any client computer or terminal capable and authorized for such access (via, for example, a web browser). The client computer/terminal may then be employed to control an appropriate stimuli generator and to gather responses from the test subject. To facilitate testing, the downloadable computer software and data can be downloaded once and reused over and over at the client computer/terminal. Alternatively, the downloadable computer software and data can be downloaded for each individual testing session via the network as needed. In some cases, the computer software may be executed at the servers themselves, with program outputs transmitted to the client computer/terminal for interfacing with the I/O devices. Alternatively, execution may take place locally at the client computer/terminal after downloading. Data pertaining to the client's responses may be transmitted to another computer on the network to permit a remote health care professional to monitor the patient's participation and progress simultaneously or on a periodic basis. Network computing techniques and implementations therefor are well known in the art and are not discussed in great detail here for brevity's sake.

Assessment for Depression Symptoms

Figure 2:
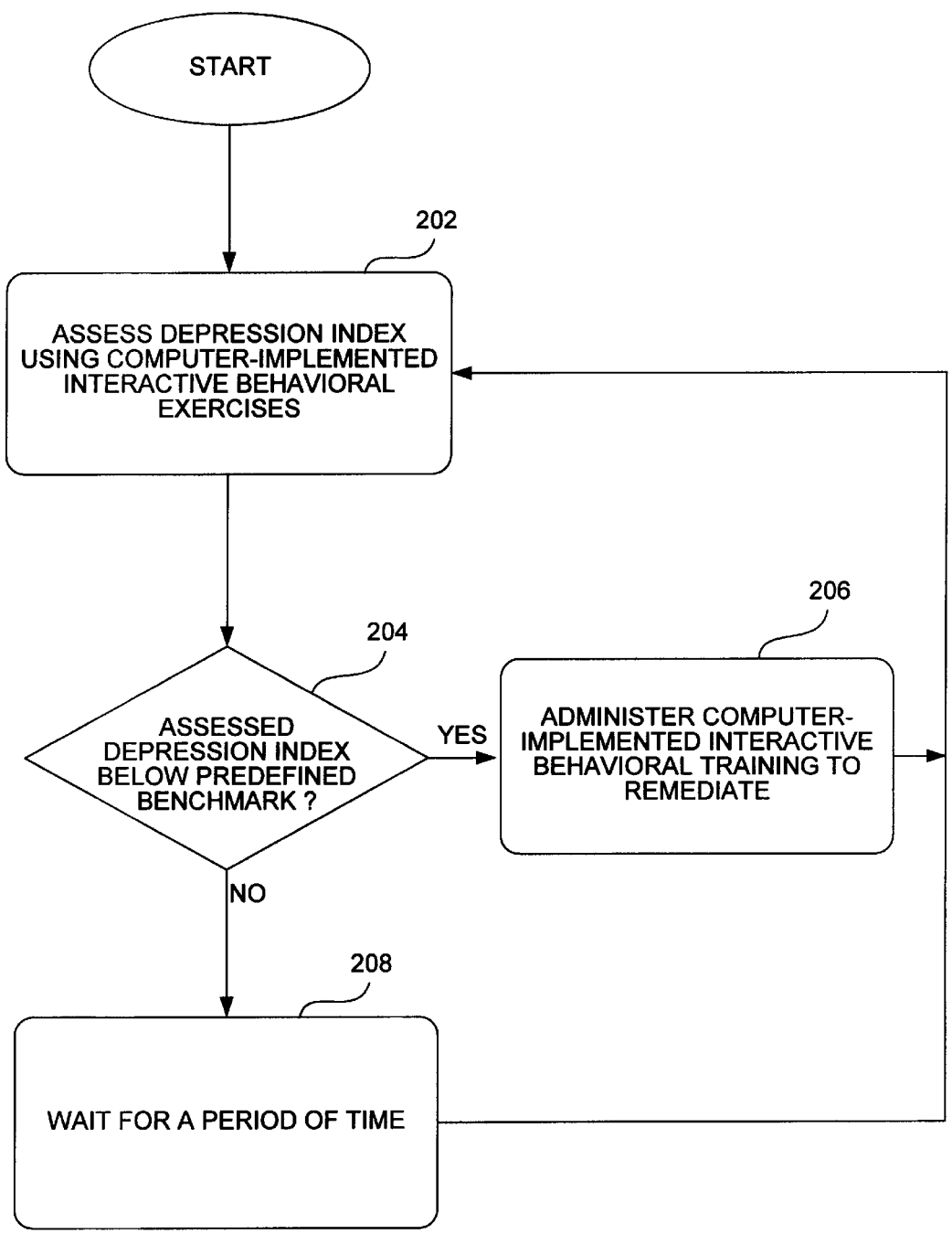
FIG. 2 illustrates some exemplary computer-implemented interactive behavioral training exercises that may be administered to a subject for depression risk assessment.

FIG. 2 illustrates, in accordance with one aspect of the present invention, the inventive method for employing interactive behavioral exercises to assess depressive symptoms in subjects on an ongoing basis and if appropriate, employ interactive behavioral training to remediate or as a prophylactic. In step 202, the interactive behavioral exercises are administered to a subject using computer-implemented behavioral interactive exercises. In the typical scenario, the interactive behavioral exercises are administered to those suspected to be suffering from depression or those who have suffered depression in the past but may need on-going monitoring to prevent recurrence, or in those that may be at risk for initial depression onset. The subject's performance on the computer-implemented interactive behavioral exercises is then compared against a predefined benchmark (204). The predefined benchmark may be, for example, the performance expected of a normal or the minimal performance below which degraded abilities are indicated. The exact benchmark of course depends on the nature of the exercises administered.

If the subject's performance is below the predefined benchmark, interactive behavioral training is administered, using computer-implemented interactive behavioral training exercises, to remediate (step 206). After training, the subject may be tested again in step 202 to ensure that sufficient progress has been made. Additional training may be required (loop 202/204/206) until the subject's performance increases.

Alternatively, if the performance is above the predefined benchmark, the subject may be retested after a period of time (step 208) to permit the subject to be monitored for depression risk over time. In this manner, the assessment steps of FIG. 2 employ the performance results of the interactive behavioral exercises to define and maintain a safe operational position on an on-going basis.

Based on the conceptual foundations and within the general guidelines discussed herein, the exact interactive exercises employed for the assessment of depression symptoms could vary greatly. In each of the examples below, the subject's performance may be documented by the computer either response by response or over the course of the assessment regime, to allow the health professional (either manually or via software) to gauge the subject's performance relative to normals.

By way of example, one assessment regime may be designed to assess the subjects' responses to novel stimuli. The subject may receive through the computer a base list of words, or alternatively, a basic scene. They are instructed to respond to the computer, e.g., by a computer mouse button press or by a conventional or special keyboard or other interface device reaction, as soon as they hear a word that has not been presented before, or as soon as a new object or character appears in the action scene they are viewing. The word list and scene can progressively expand into a long list of words or objects. Subjects will be evaluated on the number of novel stimuli that they find, as well as their reaction times in finding the stimuli.

As another example, another computer-implemented assessment regime may be designed to assess the subjects' willingness to take novel decision paths ('novelty-seeking'). The subject may be asked to work at a sentence completion task after a list of initially repetitive "correct" sentences are presented by the computer. The subject may then be tested at a sentence completion task through the computer in which he/she is asked to insert a word from a choice list including rehearsed-word and novel word answers. Choice lists may be varied with respect to the similarity or substitutional validity of "novel" words to "correct" (rehearsed) words. Equivalent novelty-seeking measures can be implemented in a real-world model behavior-alchoice assessment format through the computer. Subjects will be evaluated on their probability of choosing a familiar stimulus.

As yet another example, another computer-implemented assessment regime may be designed to assess the subjects' performances at a 'vigilance' task, again with measures of their reaction times in responding to target stimuli. The subject may be given a target word through the computer, and must respond to the computer as fast as possible every time the word occurs, against a background of other (foil) words presented by the computer. Foil (non-target) and target words are presented by the computer at a series of presentation rates, with a variation in the rate of occurrence of target words, and in a series in which background non-target words increase in their number and their perceptual confusability with target words. Target words may also be presented by the computer with random positions of occurrence. The same class of test may be implemented with the presentation of target pictures or objects or written words or numbers on the computer screen, rather than with aurally presented words or other speech stimuli.

As yet another example, another computer-implemented assessment regime may be designed to assess the subjects' reactions to fear-inducing ('harm-avoiding') stimuli. By way of example, a computer-implemented assessment regime may be constructed in a form similar to standard interview assessments used to measure 'harm-avoidance', e.g., the harm-avoidance component of the Cloninger Tri-dimensional Personality Questionnaire.

As yet another example, a computer implemented assessment regime may be designed to use the combination of short term memory and reaction time deficits known to be present in depression. The subjects can be shown sets of pairs of objects, each of which may be a word, or symbol, or image. The subjects are then given a series consisting only of one of each pair of object, and are asked to create the corresponding series based on the second of each pair of objects. Subjects are scored based on the speed and accuracy with which they create the target sequence.

Figure 3:
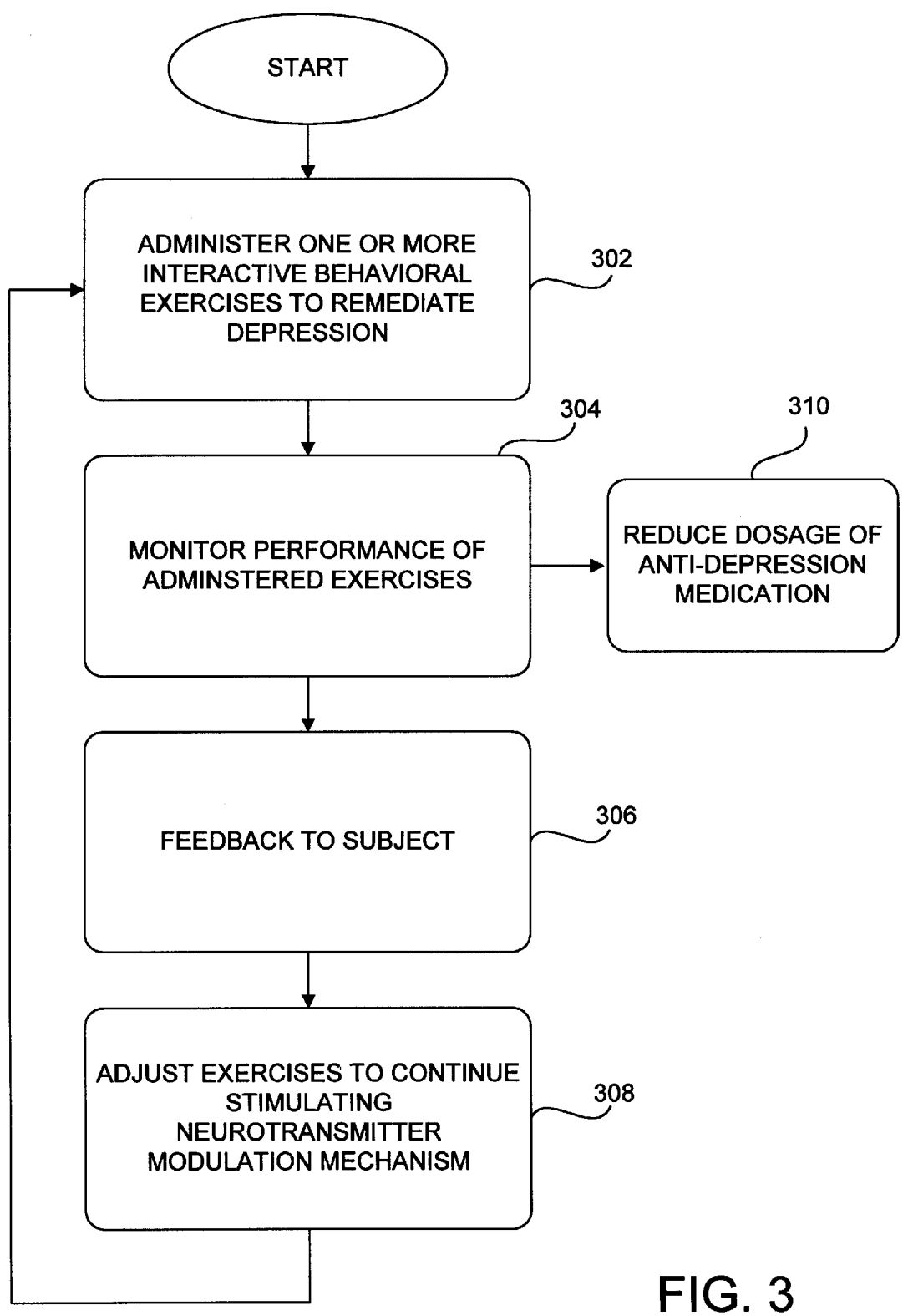
FIG. 3 illustrates, in accordance with one embodiment of the present invention, the steps involved in using interactive behavioral training to remediate depression.

FIG. 3 illustrates, in accordance with one embodiment of the present invention, the steps involved in using computer-implemented interactive behavioral training to remediate depression in human subjects. The interactive behavioral exercises are administered in step 302 to the subject.

In general, the behavioral training exercises are administered with a relatively high intensity (many behavioral response trials/hour) for substantial periods each day (preferably 1–3 or more hours) and repeated over many successive days to drive progressive neurological changes that affect the target neurotransmitters involved in the distribution of, among others, norepinephrine and serotonin. The training exercises are chosen to be rich in novelty and surprises as that results in norepinephrine release and increases overall brain activity, which leads to an increase in serotonin release. Further, the exercises are preferably designed to engage the cortex (and locus coeruleus) in intensive tasks in which expected or target outcomes are achieved, because that is believed to result in a progressive strengthening of norepinephrine release on a heavy schedule.

While full of interest and novelty, the exercises are preferably chosen to be calming, relaxing and quieting, focusing on positive occurrences, positive social behaviors and reactions, since the amelioration of stress-induced reactions is one of the training goals. As the training regime progresses, the exercises should naturally impel the subject to respond with progressively faster reaction speeds because slow reactions in cognitive responses are a common aspect of behaviors in depressives that can be ameliorated by interactive behavior training.

In step 304, the subject's performance in the interactive training exercises are monitored for performance and improvement. The subject's trial-by-trial and overall progress for each session or each day may be recorded by the computer and provided to a supervising health care professional (e.g., a supervising psychiatrist or therapist), who may be informed on the same computer or at a remote computer through the computer network (e.g., a LAN, WAN, or the Internet). In this manner, the health care professional may be able to work with multiple subjects at once and may not need to be physically present. By monitoring the subject's progress, the health care professional may be informed about subject compliance and can intervene if the subject is not complying (which is common for depressives as they may be less than motivated in undertaking training regimes), is not working at the training exercises in the appropriate manner or is stalled (and therefore may require special assistance or switching to a different set of exercises).

Note that this monitoring may be performed throughout the exercises to facilitate varying the exercises to maintain interest and/or novelty, while ensuring that positive reinforcements are given for achieving short-, intermediate-, and long-term training goals.

In step 306, feedback is preferably given to the subject pertaining to the subject's performance. Feedback should focus on the positive, with a de-emphasis on significant negative feedback. If the subject makes an error, there is preferably a significant step back in task difficulty since depressives tend to have exaggerated responses to negative reinforcement and high repetitive failure rates re common problems in the behaviors of depressives. As mentioned, the interactive training exercises are preferably chosen so that the subject is correct and rewarded a substantial percent of the trials attempted (with some relevant rewards, which may be intangible such as an audible or a visual presentation signaling a correct response, or a game, or more tangible rewards such as points or tokens that may be redeemable for cash, prizes, etc.). The rich trial-associated rewards are believed to result in further trial-by-trial coeruleus neuron response (e.g., norepinephrine release). Additionally, the positive feedback and/or rewards are intended to encourage subjects to be goal-oriented since it has been known that depressives have difficulties in maintaining goal-directed behaviors.

Optionally, the present inventive training technique may be employed as an adjunct to conventional pharmacological approaches to treating depression. That is, the improvement provided by the interactive training may reduce or eliminate the dosage of anti-depression drugs required for treating depressives (step 310), or may extend or elaborate the positive treatment effects of the drug. The reduction may be performed according to dynamic tailoring techniques. Dynamic tailoring of dosages is discussed in detail in a commonly owned, co-pending patent application entitled "Methods And Apparatus For Dynamically Tailoring Biochemical Based Therapy Programs In Human", filed by inventors Steven L. Miller, Michael M. Merzenich, and Bret E. Peterson on Jun. 18, 1998 (Attorney Docket No. STLCP004, application Ser. No. 09/100,663) which is incorporated by reference herein. Thus, the subject's depression symptoms may be brought under control more quickly through a combination of anti-depression drugs and interactive training, with the dosages of the anti-depression drugs steadily decreasing over time as the monitored performance improves.

As mentioned earlier, the interactive behavioral exercises are designed such that there is intensity as well as richness in novelty and surprises while at the same time ensuring that the patients are substantially rewarded for correct performances a substantial percent of the time (e.g., about 80% or more in one embodiment). Accordingly, the exercises are preferably adjusted automatically by the computer in step 308, responsive to the monitoring of step 304, to keep the tasks interesting and novel. In one example, the subjects operate on a on a 3-up, 1-down staircase or other learning progression designed to assure that they get the substantial majority of trials "correct", e.g., when they get three "answers" correct in a row, the task becomes more difficult by one small difficulty step; while when they get one "answer" incorrect, the task becomes easier, by one difficulty step or more preferably becomes easier by a larger backward than forward difficulty step to prevent exaggerated responses to negative reinforcement and high repetitive failure rates.

Subjects may be rewarded not only when they get each correct answer, but also when they reach a particular task benchmark difficulty level. Subjects may work for predefined performance goals, and may be rewarded when they reach goals and subgoals. At the end of each training session, they may be informed about their progress toward reaching those goals. As mentioned, the emphasis on intensity, novelty/surprises, rewards and positive feedback is designed to stimulate the release of neurotransmitters in the forebrain to facilitate plastic neurological changes that will be enduring in character.

Additionally, it is preferable that a high number of trials per day be administered. By way of example, hundreds or thousands of trials per day may be administered to the subject to ensure that the neurochemical modulation mechanism is sufficiently stimulated. It is contemplated that training may last at least one hour per day and may extend to as many hours as necessary, limited only by the subject's interest level, stamina, and attentional focus. In general, about 1 to 3 hours per day may be devoted to training.

The exact number of trials depend on many factors, including the length of each trial (e.g., a story will take longer to absorb than a set of stimuli consisting of two audible words), the attentional focus required (which limits the mental endurance of the subject), and the like. These trials may relate to a single skill or to different skills to be trained during the training day. The training of all relevant skills may take place during a single day or on different days. It is preferable, although not absolutely necessary, that training be performed every day to ensure continued progress. Irrespective of the exact format, the intensive interactive behavioral exercises are configured to be sufficiently intensive in the number of trials to fundamentally change the expression of neurotransmitter in the brain to address the neurochemical imbalance believed to underlie depression. In this respect, the result sought and achieved is different in kind than that achieved by the prior art piecemeal training approach in which such intensiveness is either lacking or unnecessary to achieve improvement by rote in a specific skill. Some exemplary training exercises that may be employed to remedy depression are discussed later herein.

Within the general guidelines discussed herein, the exact interactive exercises that would work effectively could vary greatly. Thus, the exercises listed below should be viewed as exemplary and not limiting of the scope of the present invention.

Vigilance training I: Printed or aurally presented words or visual objects are used as targets against foil (non-target) strings of other printed or aurally presented words, or visual objects. The subject will work at a task difficulty level in which most (about 80%) answers are correct. As the subject progresses in their performance by correctly identify target words with high probability, task difficulty is increased to maintain an approximately constant correct-answer level. Correct trials are associated with multiple forms of positive reinforcement (positive sounds, encouraging verbal responses, lights and other success signals, performance barometers, points convertible to "prizes" or other rewards in a token economy, etc. Task difficulty is varied by altering the rate of occurrence of target words (or objects), the rate of presentation of foil and target words (or visual objects), the numbers of target words or objects that signal a response, the numbers of foil words, the perceptual and semantic similarities of foil and target words, and so forth. The subjects work for intermediate and long-term (end-of-exercise-level) goals, and are continually informed of their progress toward those goals. Words chosen for use promote positive affect; few to none of the negative effect-inducing words are used. Performance barometers preferably move only in positive directions.

Vigilance training II. Words or phrases or concepts as targets in narrative (calming, quieting) stories. In this example exercise, the subject interacts with positive, calming content animated stories, and is asked to identify recurring words, phrases or emotionally-labeled events.

Novelty detection against multiple backgrounds. In this variation of a vigilance task, the subject performs a variety of "odd-man-out performance tasks, again with presentation word lists or objects both connected to visual scenes. The subject will receive a repetitive stream containing 1–20 or more objects or words, and will be required to respond whenever a novel object or word is presented. Response (reaction) time will again be monitored, and subject's accumulated rewards will reflect response times. Game control and task difficulty variations parallel those applied in Vigilance training I exercises. As with Vigilance training I, this task can be imbedded in a continuous performance task, e.g., in which the rate or success of advance of an active character(s) in the "game" is controlled by the correct response rate for the subject.

Alternative novelty detection. In this second version of an "odd-man-out" novelty detection exercise, we create an object and word-enriched environment filled with novelty. The subject operates in this world to identify new novel objects or events, against a background that progressively expands its complexity (i.e., the list of familiar objects and orally presented information expands) as more and more of the world is revealed to the subject. Again game control and reward strategies are as applied in Vigilance training I and Novelty detection tasks described earlier.

Short-term memory/prediction training. In this example task the subject is briefly presented with aurally presented model sentences or visual scenes; then after a variable-duration delay, is engaged in a sentence or scene "completion" task, given alternative words and figures with which to complete the sentence or scene. The object can be a part (s) of a picture or word "puzzle". Alternatively, a single or multiple words or a puzzle "piece" can be briefly presented; then after a delay, must be correctly inserted in a correct sentence or open puzzle space. Task difficulty is varied by changing the target exposure and target-scene exposure times, by altering the sizes, simplicities and numbers of remembered targets, by increasing the complexity of puzzle/ sentence backgrounds. Again, game control and reward strategies are as applied in above-described exercises.

While this invention has been described in terms of several preferred embodiments, there are alterations, permutations, and equivalents which fall within the scope of this invention. It is therefore intended that the following appended claims be interpreted as including all such alterations, permutations, and equivalents as fall within the true spirit and scope of the present invention.

What is claimed is:

1. A computer-implemented method for remediating depression in a person, comprising:
   (a) assessing, using a computer-implemented interactive behavioral assessment regime, a depression index for said person;
   (b) if said depression index is above a predefined benchmark, periodically reassessing said depression index by
      waiting for at least a predefined period of time, and
      performing (a) after said predefined period of time expires; and
   (c) if said depression index is below said predefined benchmark, treating said person by administering computer-implemented interactive behavioral training to said person, said computer-implemented interactive behavioral training being sufficiently intensive during each training day to create an enduring change in modulatory functions of neurotransmitters of at least one of norepinephrine and serotonin in said person.

2. The computer-implemented method of claim 1 wherein said computer-implemented interactive behavioral training is configured to permit said person to be correct in at least 50% of the training administered.

3. The computer-implemented method of claim 2 wherein said computer-implemented interactive behavioral training is configured to permit said person to be correct in at least 80% of the training administered.

4. The computer-implemented method of claim 1 wherein administering said computer-implemented interactive behavioral training includes administering a set of computer-implemented exercises.

5. The computer-implemented method of claim 4 further including adjusting said set of computer-implemented exercises.

6. The computer-implemented method of claim 5 further including adjusting said set of computer-implemented exercises based on a correction staircase.

7. The computer-implemented method of claim 5 further including adjusting said set of computer-implemented exercises such that the person is required to respond with progressively faster reaction speed.

8. The computer-implemented method of claim 4 wherein the number of exercises in said set of computer-implemented exercises is sufficient to change the expression of a neurotransmitter which underlies depression.

9. The computer-implemented method of claim 8 wherein administering said computer-implemented interactive behavioral training includes at least one hundred exercises during each training day.

10. The computer-implemented method of claim 4 wherein said set of computer-implemented exercises includes a vigilance task.

11. The computer-implemented method of claim 4 wherein said set of computer-implemented exercises includes a novelty task.

12. The computer-implemented method of claim 4 wherein said set of computer-implemented exercises includes a short-term memory task.

13. The computer-implemented method of claim 1 wherein administering said computer-implemented interactive behavioral training is on a daily basis.

14. The computer-implemented method of claim 1 wherein administering said computer-implemented interactive behavioral training is performed for at least one hour per day.

15. The computer-implemented method of claim 1 further including providing feedback to said person.

16. The computer-implemented method of claim 1 wherein said computer-implemented interactive behavioral training is further directed to upregulate modulatory functions of dopamine and acetylcholine.

17. The computer-implemented method of claim 1 wherein said computer-implemented interactive behavioral training is further directed to include substantial novelty and surprise.

18. The computer-implemented method of claim 17 wherein said computer-implemented interactive behavioral training is further directed to include calming said person.

19. The computer-implemented method of claim 1 wherein said computer-implemented interactive behavioral training is further directed to enliven the cerebral cortex to improve its level of arousal.

20. The computer-implemented method of claim 19 wherein said computer-implemented interactive behavioral training is further directed to improve ability to respond to stimuli with vigilance.

21. The computer-implemented method of claim 1 wherein administering said computer-implemented interactive behavioral training is performed prophylactically.

22. The computer-implemented method of claim 1 wherein administering said computer-implemented interactive behavioral training is performed in as an adjunct to a pharmacological approach to remediating depression.

23. The computer-implemented method of claim 1 further including rewarding, using said computer-implemented approach, said person.

24. The computer-implemented method of claim 1 wherein administering said training is performed using one of a LAN, a WAN or the Internet.

25. A computer-implemented method for assessing depression for person said method comprising:
   (a) administering, using said computer-implemented approach, a set of behavioral assessment exercises to said person, said set of behavioral assessment exercises being / configured to determine a depression index for said person;
   (b) comparing said depression index against a predefined benchmark; and
   (c) repeating (a)–(b) periodically.

26. The computer-implemented method of claim 25 further including reporting said depression index to a health professional.

27. The computer-implemented method of claim 26 wherein reporting said depression index to said health professional uses the Internet.

28. The computer-implemented method of claim 25 wherein administering said set of behavioral assessment exercises is done in conjunction with a treatment for depression.

29. The computer-implemented method of claim 28 wherein said treatment for depression is biochemically based.

30. The computer-implemented method of claim 25 wherein said person has suffered from depression in the past.

31. The computer-implemented method of claim 25 wherein said set of behavioral assessment exercises include one of assessing the person's response to novel stimuli, vigilance stimuli, and fear-inducing stimuli.

32. The computer-implemented method of claim 25 wherein said set of behavioral assessment exercises is designed to assess the person's short-term memory.

33. A computer readable medium including instructions for remediating depression in a person, said computer-implemented medium comprising:
   (a) instructions for assessing, using a computer-implemented interactive behavioral assessment regime, a depression index for said person;
   (b) instructions for if said depression index is above a predefined benchmark, periodically reassessing said depression index by
      waiting for at least a predefined period of time, and
      performing (a) after said predefined period of time expires; and
   (c) instructions for, if said depression index is below said predefined benchmark, treating said person by administering computer-implemented interactive behavioral training to said person, said computer-implemented interactive behavioral training being sufficiently intensive during each training day to create a permanent change in modulatory functions of neurotransmitters of at least one of norepinephrine and serotonin in said person.

34. A computer implemented method for delivering computer readable instructions for remediating depression in a person, said computer-implemented method comprising:
   (a) transmitting, over a signal transmission medium, signals representative of instructions for assessing, using a computer-implemented interactive behavioral assessment regime, a depression index for said person;
   (b) transmitting, over a signal transmission medium, signals representative of instructions for if said depression index is above a predefined benchmark, periodically reassessing said depression index by waiting for at least a predefined period of time, and performing (a) after said predefined period of time expires; and (c) transmitting, over a signal transmission medium, signals representative of instructions for, if said depression index is below said predefined benchmark, treating said person by administering computer-implemented interactive behavioral training to said person, said computer-implemented interactive behavioral training being sufficiently intensive during each training day to create an enduring change in modulatory functions of neurotransmitters of at least one of norepinephrine and serotonin in said person.

35. A computer-implemented method for reducing the effects of depression for a human subject, said computer-implemented method comprising:

administering, using said computer-implemented approach, a training regime including at least one behavioral test to said human subject, said training regime being configured to substantially augment the behaviorally appropriate release of modulatory neuotransmitters associated with at least one of remediating depression and the clinical symptoms of depression;

obtaining, using said computer-implemented approach, a performance response of said human subject in said at least one behavioral test; and altering, using said computer-implemented approach, testing parameters pertaining to said at least one behavioral test, wherein said altering of said testing parameters facilitates substantially augmenting the behaviorally appropriate release of modulatory neuotransmitters associated with at least one of remediating depression and the clinical symptoms of depression.

36. The computer-implemented method of claim 35 wherein the at least one behavioral test calms the subject.

37. The computer-implemented method of claim 35 wherein the behaviorally appropriate release of modulatory neuotransmitters includes the behaviorally appropriate release of at least one of seratonin, norepinephrine, doparine and acetycholine.

* * * * *